(12) United States Patent
Kathe et al.

(10) Patent No.: US 9,535,048 B2
(45) Date of Patent: Jan. 3, 2017

(54) METHOD FOR DETERMINING NUMBER OF DROPS

(75) Inventors: Ulrich Kathe, Ludwigsburg (DE); Oliver Bettmann, Russelsheim (DE)

(73) Assignee: Endress + Hauser Conducta GmbH + Co. KG, Gerlingen (DE)

( * ) Notice: Subject to any disclaimer, the term of this patent is extended or adjusted under 35 U.S.C. 154(b) by 912 days.

(21) Appl. No.: 13/258,262

(22) PCT Filed: Mar. 15, 2010

(86) PCT No.: PCT/EP2010/053266
§ 371 (c)(1),
(2), (4) Date: Sep. 21, 2011

(87) PCT Pub. No.: WO2010/108801
PCT Pub. Date: Sep. 30, 2010

(65) Prior Publication Data
US 2012/0028361 A1    Feb. 2, 2012

(30) Foreign Application Priority Data
Mar. 25, 2009    (DE) .................. 10 2009 001 860

(51) Int. Cl.
G01N 35/00    (2006.01)
G01N 33/18    (2006.01)
(Continued)

(52) U.S. Cl.
CPC ............ *G01N 33/1846* (2013.01); *G01N 7/18* (2013.01); *G01N 35/1016* (2013.01);
(Continued)

(58) Field of Classification Search
CPC ............ G01N 7/18; Y10T 436/179228; Y10T 436/204998; Y10T 436/115831
(Continued)

(56) References Cited

U.S. PATENT DOCUMENTS 5,637,787 A    6/1997    Fukushima et al.
6,469,780 B1 *  10/2002    McDermott et al. ........... 356/37
8,932,873 B2    1/2015    Kathe

FOREIGN PATENT DOCUMENTS

DE    4344441    7/1995
DE    19617910    11/1997
(Continued)

OTHER PUBLICATIONS

German Search Report in corresponding German Application No. 102009001860.3.
(Continued)

*Primary Examiner* — Rebecca M Fritchman
(74) *Attorney, Agent, or Firm* — Christopher R. Powers; PatServe

(57) ABSTRACT

A method for determining the number of drops metered with a drop frequency into a reactor, especially in a high temperature decomposition system for analyzers, wherein a gas stream is flowing through the reactor. There exists in the reactor a temperature, which is greater than the boiling temperature of the liquid, and a drop metered into the reactor transforms at least partially into the gas phase following entry into the reactor, especially due to heat transfer from contact with a surface within the reactor, especially directly after contact with the surface within the reactor. With a sampling rate, which is greater than the drop frequency, a sequence of pressure signals dependent on pressure within the reactor is registered, and, from the sequence of pressure signals or from values derived therefrom, the number of drops metered into the reactor is ascertained.

14 Claims, 3 Drawing Sheets

(51) Int. Cl.
    *G01N 7/18* (2006.01)
    *G01N 35/10* (2006.01)
    *G01N 25/00* (2006.01)
(52) U.S. Cl.
    CPC ............... *Y10T 436/115831* (2015.01); *Y10T 436/179228* (2015.01); *Y10T 436/204998* (2015.01)
(58) Field of Classification Search
    USPC .......................... 436/50, 133, 118; 411/178
    See application file for complete search history.

(56) References Cited

FOREIGN PATENT DOCUMENTS

| | | |
|---|---|---|
| DE | 10127353 | 12/2002 |
| DE | 102006058051 | 6/2008 |
| EP | 0237773 | 9/1987 |
| JP | 59-188523 | 10/1984 |
| WO | 2008068196 A1 | 6/2008 |

OTHER PUBLICATIONS

International Search Report in corresponding International Application No. PCT/EP2010/053266 dated Jun. 23, 2010.
English translation of the International Preliminary Examination Report.

\* cited by examiner

METHOD FOR DETERMINING NUMBER OF DROPS

TECHNICAL FIELD

The present invention relates to a method for determining the number of drops metered with a drop frequency into a reactor, especially in a high temperature decomposition system for analyzers.

BACKGROUND DISCUSSION

The dropwise dosing of liquids into a reactor plays a role in analytical technology, for example. Frequently, in such applications, analytes or reagents need to be dosed. The dropwise dosing of liquids should generally fulfill the purpose of introducing a defined volume of a substance into the reactor.

For example, an application important for waste water analysis, in the case of which the analyte is to be metered dropwise into a reactor, is the determining of carbon content and/or nitrogen content in wastewater, for example, the TOC (Total Organic Carbon, total organically bound carbon) or the $TN_b$ (Total Nitrogen, total bound nitrogen). In the case of known methods for determining these parameters, a liquid sample of small volume of, for example, some 100s of μl is fed dropwise to a reactor of a high temperature decomposition system. In the reactor, which, for example, is provided by a high temperature reactor formed as a pyrolysis tube, the organic ingredients are thermally decomposed to $CO_2$ and the nitrogen containing ingredients to nitrogen oxide $NO_x$. The acronym $NO_x$ stands here for a mixture of nitrogen oxides with nitrogen in different degrees of oxidation, which, however, has NO as the main component. In the decomposition in the high temperature reactor, there arises a gas mixture, which besides $CO_2$ and $NO_x$ contains gaseous $H_2O$ and, in given cases, other pyrolysis- and reaction products of substances contained in the sample. The gas mixture is, with the assistance of a carrier gas (which, as a rule, also delivers the oxygen needed for the reaction) flowing permanently through the reactor, transported through a cooler having a water separator, a gas filter and an analytical unit. The amount of the occurring $CO_2$, or $NO_x$, is determined, for example, by infrared measurement or by chemiluminescent measurement, and, therefrom, the TOC—, or $TN_b$ content of the liquid sample determined.

The temperatures reigning in the high temperature decomposition system lie during operation significantly above the boiling point of the dosed liquid sample. In the case of TOC— or $TN_b$ determination, there rules in the interior of the reactor usually a temperature of about 650° C. up to 1300° C., depending on whether the decomposition of the sample is supported supplementally by a catalyst. In contact with the wall of the reactor or other surfaces present within the reactor, a liquid drop reaches, within a very short time, boiling temperature and, respectively, the reaction temperature required for the reaction with the oxygen contained in the carrier gas. A liquid drop dosed into the reactor transforms into the gas phase, consequently, directly after the dosing, by evaporation and/or by forming gaseous reaction products.

In determining the analyte concentration, for example, the TOC— or $TN_b$-value, it is necessary to know the volume of the sample liquid metered into the reactor exactly. Especially, in the case of small sample volumes in the μl-, or lower ml-range, defective metering can lead to intolerable departures of the ascertained analyte concentration from the actually present analyte concentration. If one assumes, for example, that a volume of 400 μl of an aqueous solution corresponds, for instance, to 20 drops, then there results in the case of a defective dosing, in the case of which only 19 drops were metered into the reactor, already a deviation of the actually dosed sample volume from the predetermined sample volume of around 5%.

Defective metering can, however, exactly in automated operation of an analytical apparatus, occur again and again, for example, by plugging of the sample supply line by solid particles contained in the sample or due to gas bubbles in the sample to be metered. It is, consequently, desirable, for assuring a correct analytical result, to monitor the metering of the sample into the reactor.

In infusion technology, for example, from EP 237773 A1, it is known to detect drops by optical means, for example, by light barriers, and, in this way, to monitor, how many drops of a liquid are actually dosed. Such an apparatus is, however, structurally complex, and especially as regards the described applications in the high temperature range only difficultly implemented. Even when the reactor of the high temperature decomposition system is transparent, for example, formed from quartz glass, and the light barrier is arranged outside of the pyrolysis tube, such a monitoring of the dosing of drops into the pyrolysis tube is not practical, since the transparency of the quartz glass decreases over the duration of operation due to the deposition of salts and through local crystallization of the quartz glass matrix through the influence of alkalai metal ions at high temperatures.

SUMMARY OF THE INVENTION

It is, consequently, an object of the invention to provide a method for determining the number of drops of a liquid metered into a reactor, which method overcomes the disadvantages of the state of the art. Especially, a method should be provided, with which the number of drops of a liquid metered into a reactor can be determined with high accuracy, and which is suitable especially for applications, in the case of which there exists in the reactor a temperature, which is higher than the boiling temperature of the liquid.

The object is achieved by a method for determining the number of drops metered with a drop frequency into a reactor, especially in a high temperature decomposition system for analyzers, wherein a gas stream is flowing through the reactor, and wherein there exists in the reactor a temperature, which is greater than the boiling temperature of the liquid, and wherein a drop metered into the reactor transforms, at least partially, especially completely, into the gas phase following entry into the reactor, especially due to heat transfer from contact with a surface within the reactor, especially directly after contact with the surface within the reactor, wherein, with a sampling rate, which is greater than the drop frequency, a sequence of pressure signals dependent on pressure within the reactor is registered, and from the sequence of pressure signals, or from values derived therefrom, number of drops metered into the reactor is ascertained.

Since the temperature of the reactor lies above the boiling temperature of the metered liquid, a drop of such liquid transforms into the gas phase directly after entry into the reactor by evaporation and/or by forming gaseous reaction products. Especially, in the case of contact with a surface within the reactor, for example, the inner wall of the reactor or a surface of an insert arranged in the reactor, heat transfer to the drops occurs especially rapidly, e.g. within less than 0.3 s, especially within less than 0.1 s, so that the drop transforms into the gas phase directly after contact with the surface. Within the reactor, an insert can be provided, which contains a bulk good, on whose surfaces such faster heat transfer can occur for impinging drops. The transfer of the drop into the gas phase leads to a short term increase of pressure (in the following referred to as a pressure pulse) within the reactor. Since a sequence of pressure signals is registered with a sampling rate higher than the drop frequency (i.e. the number of drops metered into the reactor per unit time), it is assured that each pressure pulse effected by a drop is reflected in the registered sequence of pressure signals. In this way, thus, the drop count can be determined with high accuracy, and a deviation between the predetermined drop count to be metered and the actual number of metered drops can be detected.

The pressure signals can be registered by means of a pressure measuring transducer, which is arranged preferably within the gas stream. The terminology, "a pressure measuring transducer arranged within the gas stream" refers to a pressure measuring transducer, which is arranged at any position along the flow path of the gas stream. Preferably, this position is selected to be outside of the reactor, since lower temperatures reign there as compared to within the reactor. Flow resistances in the course of the gas stream lead to the fact that pressure changes within the reactor are also detectable by a pressure measuring transducer arranged within the gas stream outside of the reactor, for example, a pressure measuring transducer arranged within a supply line for supplying the gas stream into the reactor.

For ascertaining number of drops metered into the reactor, for a current pressure signal ($P_n$) of the sequence of pressure signals, there can be ascertained by comparison with a base pressure value ($P_{average}$) a pressure change ($P_{delta}$) associated with the current pressure signal ($P_n$), and the pressure change ($P_{delta}$) compared with a predetermined threshold value. On the basis of a result of the comparison, it can be registered whether the pressure change ($P_{delta}$) corresponds to a pressure pulse effected by metering a drop into the reactor.

In such case, the base pressure value ($P_{average}$) can be formed by average formation, especially by sliding average formation, using at least two pressure signals preceding the current pressure signal ($P_n$) in the series of pressure signals. For example, the base pressure value can be set at the beginning of the method using the pressure reigning in the reactor before beginning the sample metering. During the metering of the liquid, pressure signals following one another are registered, and the base pressure value adjusted by sliding average formation taking into consideration, in each case, the most up to date pressure signals of the sequence.

If the pressure change ($P_{delta}$) exceeds the predetermined threshold value, metering of a drop into the reactor can be tallied. For registering a drop, the number of drops metered into the reactor stored, for example, in a counter can be incremented by one.

In order to prevent that the base pressure value $P_{average}$ be set too high, it can be of advantage, in the case of exceeding the predetermined threshold value, not to use the current pressure signal ($P_n$) belonging to the corresponding threshold-exceeding pressure change ($P_{delta}$) for calculating the base pressure value ($P_{average}$). Since the base pressure value $P_{average}$ corresponds essentially to the "background pressure" reigning in the reactor when a drop event is not present, it represents the "zero line" or "baseline" of the pressure curve. Incorporating the pressure signals increased by the pressure pulse arising due to the drop would lead therefore to a too high, base pressure value. Pressure signals of the sequence not to be taken into consideration can be eliminated in the case of calculating the base pressure value $P_{average}$, for example, by means of a lowpass filter.

In order to prevent that a pressure pulse be multiple counted, it can be advantageous, in determining the drop count, not to take into consideration, pressure signals registered within a predetermined time window following a pressure signal ($P_n$) belonging to a pressure change ($P_{delta}$) associated with a pressure pulse effected by metering a drop into the reactor. Threshold value exceedings ascertained for pressure signals following such current pressure signal $P_n$ should, thus, not lead to a new tallying of the metering of a drop. In such case, it is advantageous to make the said time window sufficiently wide that the pressure change belonging to the first current pressure signal registered after expiration of the time window subceeds, or falls beneath, the predetermined threshold value. This can be effected, for example, by deactivating the counter by a control mechanism for the duration of the time window. Alternatively, a controller can also cause that, for pressure signals newly registered within the time window, the described drop counting method is not performed, i.e. that especially no difference forming between the signal value and the base pressure value and also no threshold comparison are performed. Alternatively, instead of a time window, a number of pressure signals can be predetermined, which should not be taken into consideration for determining the drop count.

The subject matter of the invention is furthermore a method for determining the concentration of an analyte, especially an oxidizable substance in a liquid sample, in the case of which the previously described method for determining a drop count metered into a reactor forms one or more of the method steps. This method for determining concentration of an analyte in a liquid sample, especially an analyte in the form of an oxidizable substance, includes the steps as follows:

operating a metering system, especially a metering system comprising a pump, in order to meter a defined liquid amount dropwise with a drop frequency via a liquid inlet into a reactor of an analytical apparatus, especially an analytical apparatus including a high temperature decomposition system, wherein a gas stream, especially a gas stream having a constant volume flow rate, is flowing through the reactor, and wherein there exists in the reactor a temperature, which is greater than the boiling temperature of the liquid, and wherein a drop transforms into the gas phase directly after entry into the reactor, especially due to heat transfer from contact with a surface within the reactor, especially directly after contact with the surface within the reactor;

determining the number of drops of the liquid sample metered into the reactor according to the previously described method;

ascertaining therefrom the metered liquid amount;

registering a measured variable correlated with the amount of the analyte; and ascertaining concentration of the analyte from the measured variable and the metered liquid amount.

The measurement signal correlated with the amount of the analyte can be, for example, a signal of an optical detector, such as the initially mentioned infrared- or chemiluminescence detector.

For ascertaining the metered sample amount, for example, the number of drops of the liquid sample metered into the reactor can be compared with a reference value. It is also possible, from the number of drops metered into the reactor, with the assistance of a drop volume known, for example, from preceding reference measurements, to calculate the total volume of the metered liquid.

The reference value can be ascertained in a reference measurement, in which a defined amount of reference liquid is metered dropwise into the reactor, and the number of drops needed for the complete metering of the reference liquid amount is registered as reference value. The reference measurement is preferably performed directly after start-up or after maintenance of the analytical apparatus, such as, for example, after the cleaning or replacing of components of the analytical apparatus, since the ascertained reference value then reflects the number of drops needed under conditions ideal for the complete metering of the reference liquid amount.

In the case of a deviation of the currently ascertained drop count from the reference value by more than a predefined threshold value, an alarm can be output. In such case, the threshold value is preferably so defined that, in the case of a threshold value exceeding, i.e. a greater deviation of the actually ascertained drop count from the reference value, the analytical method is strongly degraded in such a manner that even by means of correction calculations no reliable information can be obtained concerning the sought analyte concentration. The issuing of the alarm can trigger, for example, maintenance measures, such as cleaning the liquid intake or replacing components of the analytical apparatus.

In the case of a deviation of the currently ascertained drop count from the reference value by less than a predefined threshold value, for example, in the case of a deviation of only one or a few drops, the analytical result can be treated with a correction factor. For example, entering in the correction factor can be the quotient of the ascertained drop count and the reference value. In this way, the liquid amount actually metered into the reactor enters into the calculating of the analyte concentration, so that error based on an incorrect sample amount in the concentration calculation is prevented.

The invention includes, furthermore, an analytical apparatus for determining concentration of an analyte in a liquid sample, especially an analyte in the form of an oxidizable substance, wherein the apparatus includes a metering system, especially a metering system comprising a pump, for dropwise metering of the liquid sample into a high temperature decomposition system for decomposing the liquid sample and forming a gas mixture, wherein the high temperature decomposition system has a reactor with a liquid inlet for the liquid sample, and a gas supply means for delivery of a carrier gas, and is connected with an analysis chamber via a gas outlet, wherein during operation of the apparatus a gas stream of a carrier gas forms between the gas inlet and the analysis chamber, wherein in the direction of the gas stream before the analysis chamber, especially within the gas supply means for delivery of the carrier gas into the reactor, a pressure measuring transducer is arranged, wherein the pressure measuring transducer is coupled with a control unit for additional processing of pressure signals output by the pressure measuring transducer, and wherein the control unit includes means for performing the previously described method for determining the drop count metered into the reactor.

The control unit can be a central control unit, which controls all functions of the analytical apparatus and especially controls, or performs, the previously described method for determining the concentration of an analyte in a liquid sample. In such case, the central control unit controls especially the metering system for the dropwise addition of the liquid sample and evaluates the signals, from the detection apparatus arranged in the analysis chamber. Especially, the central control unit calculates the analytical result and outputs such. It can, however, also be embodied as a separate control unit.

Between the gas outlet of the reactor and the analysis chamber, there can be arranged in the flow path of the gas stream a filter unit for removal of solid particles from the gas stream as well as a condensing unit for condensing water from the gas stream.

The control unit includes, for example, an averaging unit, which is embodied to ascertain from the sequence of pressure signals received from the pressure measuring transducer a base pressure value, for example, by forming a time average value or a sliding average value; a subtracter, which is embodied to form and to output, from a current pressure signal received from the pressure measuring transducer and from the base pressure value, a pressure change, for example, in the form of a difference signal; a threshold detector, which is embodied to compare the pressure change with a predetermined threshold value, and in the case of a threshold value exceeding to output a signal to a counter connected with the threshold detector, which is designed, upon receipt of the signal, to increment a stored value by one.

The counter can include a reset function, which permits it to reset the stored value, which represents the drop count metered into the reactor, to zero, after the metering of the total liquid sample.

The control unit can furthermore include a memory, in which, for example, a reference value can be stored, which represents an ascertained drop count in the case of a reference measurement, in the case of which a known amount of a reference liquid is metered dropwise into the reactor.

All here, and in the following, described means of the control unit for performing the method for determining the number of drops are preferably implemented as software of a microprocessor. They can, however, at least partially, also be implemented in the form of an electronic circuit.

BRIEF DESCRIPTION OF THE DRAWINGS

The invention will now be explained in greater detail based on the examples of embodiments illustrated in the drawing, the figures of which show as follows.

DETAILED DISCUSSION IN CONJUNCTION WITH THE DRAWINGS

Figure 1:
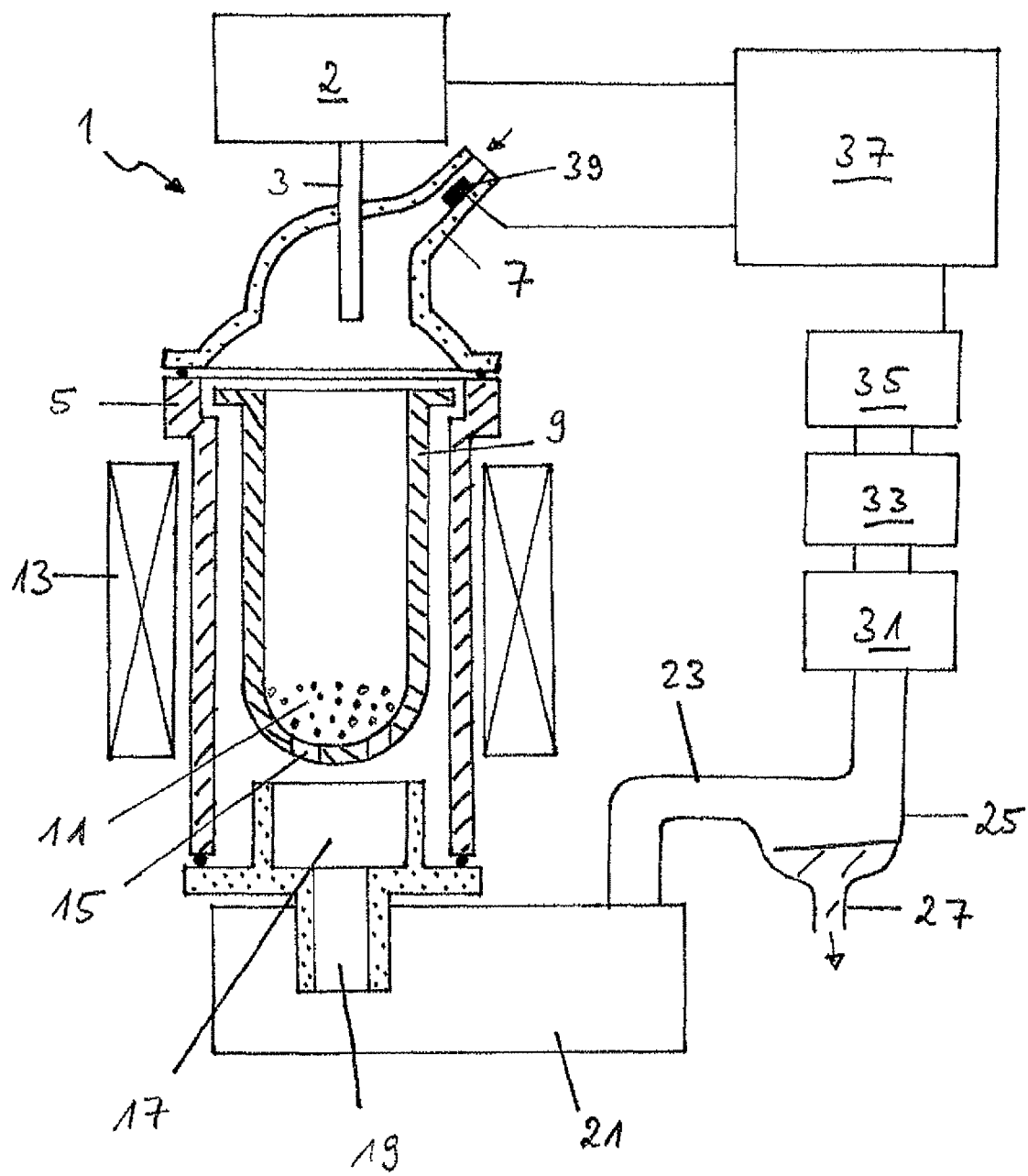
FIG. 1 is a schematic representation of an analytical apparatus for analysis of liquid samples.

In the case of the analytical apparatus 1 illustrated in FIG. 1 for determining, for example, TOC— or $TN_b$ content of a liquid sample, for example, a wastewater sample, such is fed by an only schematically illustrated metering system 2 via an injection nozzle 3 to a reactor 5 embodied, for example, in the form of a pyrolysis tube. At the same time, the reactor 5 is fed via another delivery line 7 an oxygen containing carrier gas. The reactor 5 contains in the here shown example an insert 9, which contains a catalyst 11, which supports the reaction of the liquid sample with the oxygen containing carrier gas. In order to support the reaction of the liquid sample with the carrier gas, equally, a higher inner temperature of the reactor 5 could be set. The temperature of the reactor 5 can be set by means of a heating apparatus 13 surrounding the reactor 5. In the region of the insert 9 is located the reaction zone, in which during operation a temperature between 650° C. and 1300° C. rules. Optionally, within the reaction zone, in the insert 9, a bulk good (not shown) can be accommodated, which is retained by the sieve floor of the insert 9 provided with passageways 15. In contact with a surface in the interior of the reactor, for example, with the surface of the catalyst 11 or surfaces of the bulk good, the drops of the liquid sample heat up within a very short time, namely within a few tenths of a second, especially within less than 0.4 s, to the boiling-, or reaction temperature and are transformed into the gas phase.

Beneath the insert 9, there is arranged within the reactor 5 another chamber 17, in which during operation already a lower temperature rules than in the reaction zone. At the lower end of the reactor 5 (which is directed vertically during operation), opposite the injection nozzle 3, is located a gas outlet 19, which opens into the interior of a filter unit 21, so that a gas mixture produced in the reactor 5 can flow via the passageways 15, the chamber 17 and the gas outlet 19 with the carrier gas into the filter unit 21. The filter unit 21 is connected with a condensing unit 25 via a gasline 23. The condensing unit 25 serves for the separation of water from the gas stream and is, therefore, in given cases, provided with a cooler, in order to accelerate the condensation of the water from the gas stream. The condensate is removed from the analytical apparatus 1 via line 27.

In the flow direction of the gas stream, behind the condensing unit 25, are arranged an optional drying unit 31, a further filter 33 and an analysis chamber 35. In the analysis chamber 35, the content of reaction products of the analyte, for example, $CO_2$ and/or $NO_x$, contained in the gas stream is determined. As a rule, an infrared measuring arrangement, e.g. an infrared detector, is used for determining the $CO_2$ content. For determining the $NO_x$ content, as a rule, a chemiluminescence detector is applied. The measuring signals registered in the analysis chamber 35 are fed to a control unit 37 having a computer, for example, a microcontroller or microprocessor, which, based on the measuring signals, determines the concentration of the analyte in the sample metered into the reactor 5. Control unit 37 controls, moreover, also the metering system 2 for the metering of the liquid into the reactor 5.

The entire flow path of the carrier gas is sealed relative to the environment, so that no gas can exit from the analytical apparatus 1. The gas stream exits from the analytical apparatus 1 through a gas outlet (not shown) of the analysis chamber 37. The carrier gas can alternatively also, in a circulatory process of the analytical apparatus 1, be fed back via the gas supply 7. The components of the analytical apparatus 1 following the reactor 5 represent a flow resistance for the gas stream. In this way, it is possible to detect pressure changes in the interior of the reactor 5 even in the gas supply line 7, i.e. a pressure change effected, for example, by the transforming of a metered drop into the gas phase within the reactor 5 effects a pressure change correlated therewith in the gas supply line 7. A pressure measuring transducer 39 arranged in the gas supply line 7 registers the pressure reigning in the gas supply line 7 and transduces such into an electrical signal (also referred to as the pressure signal) dependent, for example, proportionally dependent, on such pressure. From a sequence of such pressure signals, information concerning pressure changes in the reactor 5 can be developed, as explained in more detail below. The pressure measuring transducer 39 is connected on its output side with an input of the control unit 37, so that the pressure signals can be transmitted to the control unit 37. Since the entire carrier gas flow path is sealed relative to the environment, the pressure measuring transducer 39 can, for registering the pressure reigning within the reactor 5, basically be placed at any position along the flow path, for example, in the region of the gas outlet 19 or within the filter unit 21. Especially advantageously, however, the position is within the supply line 7, since there the temperature is still low, lying, for example, near room temperature.

A drop of a liquid sample metered via the injection nozzle 3 into the reactor 5 transforms into the gas phase almost directly after entry into the reaction zone, especially by heat transfer from contact with a hot surface. If the liquid sample is an aqueous solution, which, besides water, also contains oxidizable components, then, for example, the contained water transforms by evaporation into gaseous $H_2O$, while the oxidizable components, such as, for example, organic carbon- or nitrogen containing compounds, react with the oxygen containing carrier gas to form gaseous oxides, such as $CO_2$ or $NO_x$. This makes itself noticeable within the reactor 5 by a pressure pulse, which is registerable by the pressure measuring transducer 39 arranged in the carrier gas supply line 7.

Figure 2:
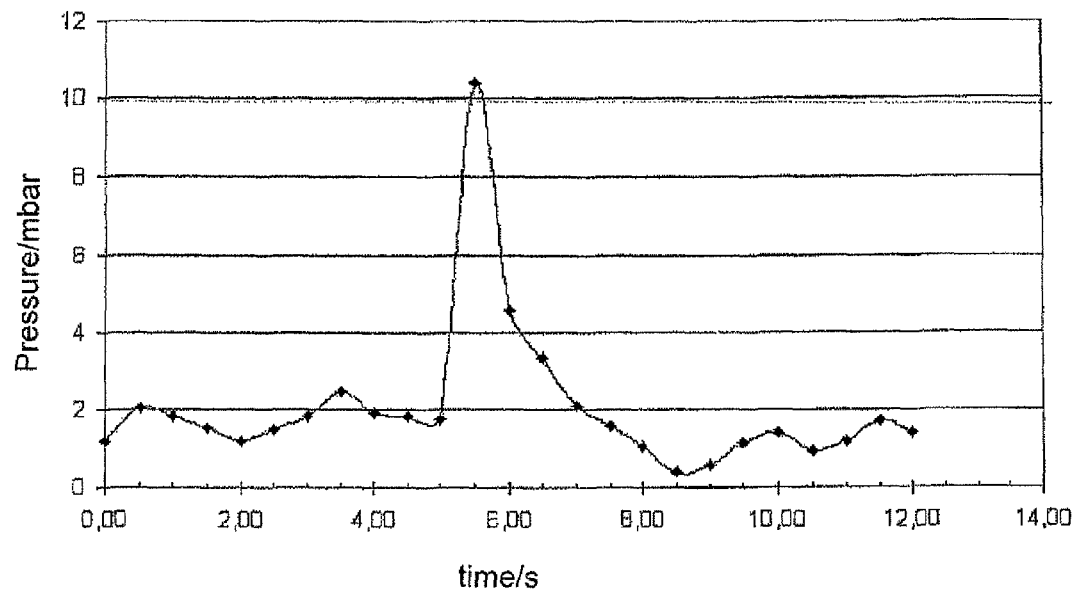
FIG. 2 shows a pressure curve within the reactor of the analytical apparatus shown in FIG. 1, in the case of metering a single drop of liquid sample.

FIG. 2 shows, by way of example, a sequence of pressure measured values, which were derived from a sequence of pressure signals output from the pressure measuring transducer 39 during the metering of a liquid drop into the reactor 5. The abscissa of the graph of FIG. 2 shows time in seconds, while pressure in mbar is measured on the ordinate. The diamonds represent the individual measured values of the sequence. As can be seen from the curve of the measured value sequence, a relatively constant pressure between 1 and just under 3 mbar is present in the reactor in the period of time between 0 and 5 s. After 5 s, a drop is metered into the reactor. This event effects a strong increasing of the subsequent, pressure measured value to a value of almost 11 mbar. After 8 s, for instance, the pressure has fallen completely back to values in the range between 0.5 and just under 2 mbar.

Figure 3:
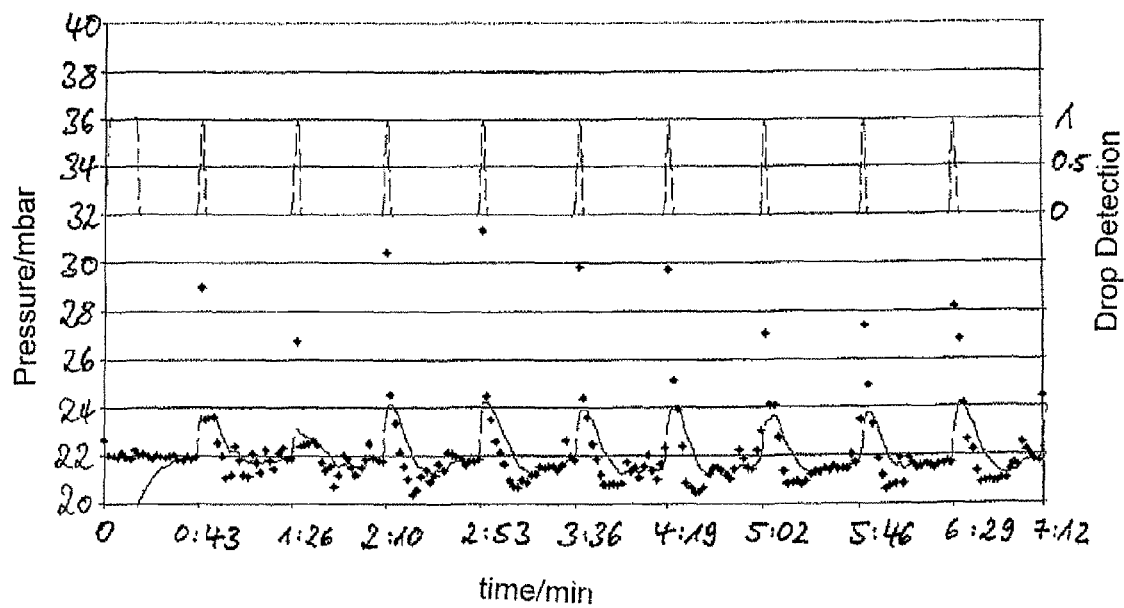
FIG. 3 shows a pressure curve within the reactor of the analytical apparatus shown in FIG. 1, in the case of metering a plurality of drops of liquid sample and detecting the individual drops.

FIG. 3 shows a sequence of pressure measured values ascertained in the case of metering nine drops with a drop frequency of about 8.6 drops/min (i.e. every 7 s a new drops is metered) into the reactor 5. Plotted on the abscissa of the shown graph is time in minutes, and, on the left ordinate, the pressure in mbar, as measured by the pressure sensor 39. The individual measured values derived from the pressure signals of the pressure measuring transducer 39 are again presented in the form of diamonds.

Evaluation of the sequence of pressure signals of the pressure measuring transducer 39 occurs by means of the control unit 37 coupled with the pressure measuring transducer 39 in the manner described in the following (compare FIG. 4): The sensor signals transduced by the pressure measuring transducer 39 and, in given cases, amplified by an amplifier 41 are forwarded, in given cases, in digitized form, to the control unit 37. The, in each case, last registered pressure signal $P_n$ is referred to in the following also as the current pressure signal. The control unit 37 includes an averaging unit 43, which forms a time average value at least of a certain number of the pressure signals of the sequence preceding the currently registered pressure signal $P_n$, for example, in the form of a sliding average value of all pressure signals registered within a predetermined time window. Equally, instead of a time window, also a certain number of pressure signals preceding the current pressure signal in the series could be predetermined. The forming of the sliding average value of at least a part of the pressure signals of the sequence preceding the current pressure signal $P_n$ is comparable to a digital low-pass filter. Correspondingly, also other comparable filter functions can be applied. The so obtained time average value forms a base pressure value $P_{average}$, which corresponds to a base pressure reigning in the reactor 5. The curve of the base pressure values versus time (dashed line) forms a type of "zero line" or "baseline" of the pressure reigning in the reactor 5. Pressure pulses due to drops transforming into the gas phase lead to an increased pressure lying above this baseline.

The baseline extends in the ideal case essentially parallel to the abscissa of the graph shown in FIG. 3. It is, however, possible that the increase of the pressure within the reactor 5 caused by a drop does not completely fall before the metering of the next drop. Likewise, a possibility is that, due to impurities in the sample gas stream, solid particles accumulate with time in the filter unit 21. Each of these circumstances leads to a gradual rise of the base pressure in the reactor 5. For being aware of the condition of the analytical apparatus 1, it is therefore possible to monitor, by means of the control unit 37, the base pressure value $P_{average}$. If the base pressure value $P_{average}$, for example, exceeds a predetermined threshold value, this can be an indication that the liquid sample is being metered too rapidly or that a plugged filter needs to be replaced. In this case, an alarm can be output, which triggers the performance of maintenance.

The control unit 37 includes, furthermore, a subtracter 45, which is coupled on the input side with the pressure measuring transducer 39 and the averaging unit 43. The subtracter forms from the respective current sensor signal $P_n$ and the base pressure value $P_{average}$ a difference signal, which corresponds to a pressure change $P_{delta}$ between the currently registered pressure signal $P_n$ and the base pressure value $P_{average}$.

A threshold detector 47 is coupled on its input side with the output of the subtracter 45, so that the difference signal $P_{delta}$ of the subtracter 45 can be transmitted to the threshold detector 47. The threshold detector 47 compares the difference signal $P_{delta}$ with a predeterminable threshold value. The threshold detector 47 is connected on its output side with a counter 49. If $P_{delta}$ lies above the predetermined threshold value, this is interpreted as a "drop event". The threshold detector 47 outputs correspondingly a signal to the counter 49, which increments the numerical value stored in the counter 49 by one. If $P_{delta}$, in contrast, lies below the threshold value, then no signal is output to the counter 49, so that the numerical value stored there remains the same. In FIG. 3, the signals of the threshold detector 47 are marked as dashed signal peaks.

Since the pressure pulses associated with the individual drops fall only after a number of pressure signals of the sequence following one after the other, there is the possibility that, per pressure pulse, not only a single, but, instead, a number of pressure signals following one after the other, or their associated difference signals $P_{delta}$ between the currently registered signals and the base pressure value, lead to a threshold value exceeding. In order to prevent that a single pulse is multiply counted, the control unit includes a function, which directly following a threshold exceeding, deactivates the threshold detector 47 for a predetermined time interval, for example, for the length of a typical rise and fall of the pressure pulse, e.g. 2 s in the example of FIG. 2. The time interval is advantageously at least so selected that the pressure change $P_{delta}$ belonging to the first current pressure signal registered after expiration of the time window safely subceeds, or falls beneath, the predetermined threshold value.

FIG. 3 shows the curve (presented as a dashed line) of the base pressure value $P_{average}$, which, in the present example, was ascertained by forming a sliding average value. When the pressure signals belonging to a pressure pulse enter in the calculation of the base pressure value $P_{average}$, there results correspondingly in the case of each new pressure pulse an extreme of the base pressure value $P_{average}$. It can, consequently, be helpful not to include in the calculating of the base pressure value $P_{average}$ those pressure signals, for which the threshold detector 47 determines that the difference signal between base pressure value and pressure signal exceeds a threshold value. In this way, pressure pulses are more safely detected as threshold exceedings of the difference signal $P_{delta}$.

In the following, a method for determining a concentration of an analyte in a liquid sample is described using the example of a TOC determination with the analytical apparatus 1 illustrated in FIG. 1.

First, a reference measurement is performed, in the case of which, under ideal conditions, for example, directly after maintenance and cleaning of the apparatus, a known amount of a reference liquid, which, as regards its drop volume influencing properties, such as viscosity, density or surface tension, is essentially the same as the liquid samples to be examined in the analytical operation, is metered dropwise into the reactor 5. In case the liquid samples are wastewater samples, the reference liquid is, for example, a sample of the wastewater in question, into which a standard substance has been mixed.

Figure 4:
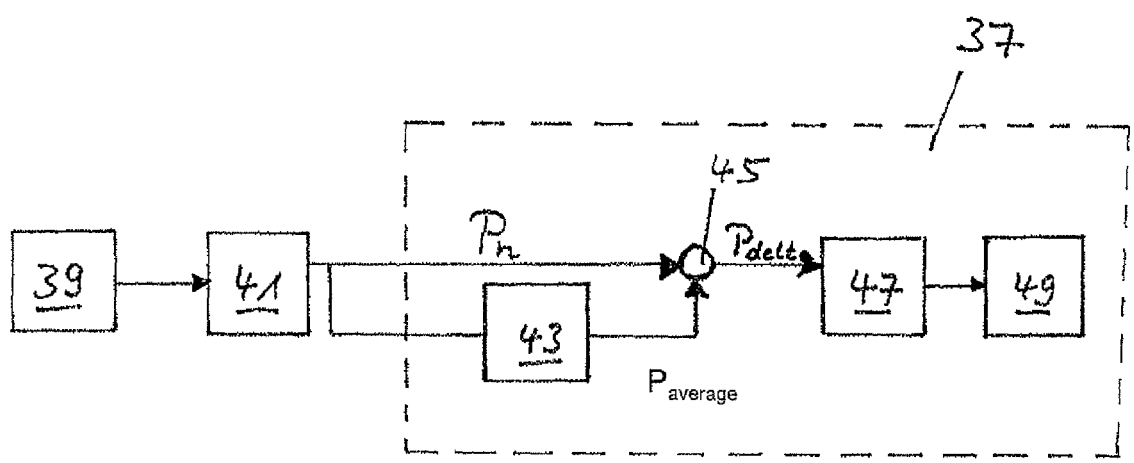
FIG. 4 is a schematic representation of a control unit for determining number of drops metered into a reactor.

The number of drops needed for metering the reference liquid is ascertained, for example, by means of the counting method described in connection with FIGS. 3 and 4. This value serves for later measurements as reference value and can be stored in a memory (not shown) of the control unit 37.

In analytical operation, the control unit 37 initiates the dropwise metering of a liquid sample into the reactor 5. For this, it issues a corresponding command to the metering system 2. At the same time, the control unit 37 sets the counter 49 to zero by means of a reset function and activates the threshold detector 47. Immediately before the beginning of the metering of the liquid sample, the base pressure value $P_{average}$ is set to a value, which represents the pressure reigning within the reactor before beginning the metering of the sample.

After beginning the metering, the earlier described counting method for determining the metered number of drops is performed. With the carrier gas stream, the oxidation products of the analyte, in the present example $CO_2$, enter the analysis chamber 35, which includes a detector, here an infrared detector, which outputs to the control unit 37 a signal dependent on the $CO_2$ content of the gas stream. The control unit 37 ascertains from the signal of the infrared detector the amount of $CO_2$ contained in the gas stream, and therefrom the analytical result, here the $CO_2$ content.

After the control unit 37 has ended the metering of the liquid sample, also the counting method is ended. The value stored in the counter 49 at this point in time is compared with the reference value gained from the reference measurement. If, in such case, there is no deviation detected between the reference value and the ascertained drop count, then the $CO_2$ content ascertained by the control unit 37 is output as the analytical result.

If there is, in contrast, a large deviation detected, for example, more than 50%, between the reference value and the ascertained drop count actually metered into the reactor 5, then an alarm is output. This alarm can serve, for example, to trigger a maintenance measure, for example, cleaning the analytical apparatus 1 or replacing components of the analytical apparatus 1.

If only a low deviation is detected between the reference value and the value stored in the counter 49, for example, a few drops, then the $CO_2$ content ascertained by the control unit 37 based on the signal of the infrared detector can be treated with a correction factor, and the corrected value output as the analytical result. The correction factor effects that the volume fraction of the sample actually present in the gas volume stream enters into the determining of the analyte content present in the gas stream. The correction factor can, for example, in the simplest case, be in the form of the quotient of the reference value and the actually metered drop count.

The invention claimed is:

1. A method for determining a number of drops of a liquid metered with a drop frequency into a reactor, comprising the steps of:
   flowing a gas stream through the reactor;
   providing in the reactor a temperature, the temperature being greater than the boiling temperature of the liquid;
   metering a drop of the liquid into the reactor;
   transforming said drop of the liquid at least partially into the gas phase following entry into the reactor;
   detecting at a sampling rate a sequence of pressure signals of a pressure measuring transducer arranged within the gas stream, said pressure signals being dependent on pressure within the reactor, wherein the sampling rate is greater than the drop frequency;
   communicating the sequence of pressure signals or values derived therefrom to a control unit; and
   calculating by means of the control unit the number of drops of the liquid metered into the reactor from the sequence of pressure signals or from the values derived therefrom.

2. The method as claimed in claim 1, wherein:
   calculating the number of drops of the liquid metered into the reactor from the sequence of pressure signals includes comparing a current pressure signal with a base pressure value and determining a pressure change associated with the current pressure signal;
   comparing the pressure change with a prescribed threshold value, and based on a result of the comparison, determining whether the pressure change corresponds to a pressure pulse effected by metering of a drop of the liquid into the reactor.

3. The method as claimed in claim 2, wherein:
   the base pressure value is obtained by computing an average value, using at least two pressure signals preceding the current pressure signal in the series of pressure signals.

4. The method as claimed in claim 2, wherein:
   the control unit registers the metering of a drop of the liquid into the reactor when the pressure change exceeds the predetermined threshold value; and
   for registering the metering of a drop of the liquid, a stored number of drops metered into the reactor is incremented by one.

5. The method as claimed in claim 2, wherein:
   in the case that the pressure change exceeds the predetermined threshold value, the pressure signal belonging to the pressure change is not used for calculating the base pressure value.

6. The method as claimed in claim 2, wherein:
   in the case that the pressure change exceeds the predetermined threshold value, pressure signals following the current pressure signal and registered within a predetermined time window do not lead to a registering of the metering of a drop of the liquid; and
   said time window is selected to be sufficiently wide that the pressure change belonging to the first pressure signal registered after the time window ends subceeds, or falls beneath, the predetermined threshold value.

7. A method for determining a concentration of an analyte in a liquid sample, comprising steps of:
   operating a metering system, comprising a pump, in order to meter the liquid dropwise with a drop frequency via a liquid inlet into a reactor of an analytical apparatus, wherein a gas stream is flowing through the reactor, and wherein a temperature within the reactor is greater than the boiling temperature of the liquid;
   determining the number of drops of the liquid metered into the reactor by transforming said drop at least partially into the gas phase following entry into the reactor due to heat transfer from contact with a surface within the reactor and
   by detecting at a sampling rate a sequence of pressure signals of a pressure measuring transducer arranged within the gas stream, said pressure signals being dependent on pressure within the reactor, wherein the sampling rate is greater than the drop frequency;
   communicating the sequence of pressure signals or signals derived therefrom to a control unit; and
   calculating by means of the control unit from the sequence of pressure signals, or from values derived therefrom, the number of drops of the liquid metered into the reactor;
   calculating by means of the control unit an amount of metered liquid therefrom;
   determining a measured variable correlated with the concentration of the analyte; and
   calculating by means of the control unit the concentration of the analyte using the measured variable and the amount of metered liquid.

8. The method as claimed in claim 7, wherein:
   calculating the amount of metered liquid includes comparing the number of drops of the liquid metered into the reactor with a reference value.

9. The method as claimed in claim 8, further including:
   determining the reference value in a reference measurement by metering a defined amount of reference liquid dropwise into the reactor, and registering the number of drops needed for complete metering of the amount of reference liquid and storing the number of drops needed for complete metering of the amount of reference liquid as the reference value in a memory of the control unit.

10. The method as claimed in claim 8, wherein:
    upon a deviation of a currently calculated number of drops from the reference value by more than a predefined threshold value, an alarm is output.

11. The method as claimed in claim 8, wherein:
    upon a deviation of a currently calculated number of drops from the reference value by less than a predefined threshold value, the ascertained concentration of the analyte is treated with a correction factor.

12. The method as claimed in claim 11, wherein:
the quotient of the currently calculated number of drops and the reference value is included in the correction factor.

13. The method according to claim 1, wherein said drop is transformed at least partially into the gas phase upon entry into the reactor due to heat transfer from contact with a surface within the reactor.

14. The method according to claim 9, wherein the reference value measurement, the determining of the reference value, and the storing of the reference value is performed directly after start up or after maintenance of the analytical apparatus.

* * * * *